(12) United States Patent
Petrinec et al.

(10) Patent No.: US 11,495,142 B2
(45) Date of Patent: Nov. 8, 2022

(54) ULTRASOUND TRAINER WITH INTERNAL OPTICAL TRACKING

(71) Applicant: SonoSim, Inc., Santa Monica, CA (US)

(72) Inventors: Kresimir Petrinec, Los Angeles, CA (US); Gabriele Nataneli, Beverly Hills, CA (US); Matthew Wang, Los Angeles, CA (US); Eric Savitsky, Malibu, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 310 days.

(21) Appl. No.: 16/777,552

(22) Filed: Jan. 30, 2020

(65) Prior Publication Data

US 2020/0242972 A1     Jul. 30, 2020

Related U.S. Application Data

(60) Provisional application No. 62/798,860, filed on Jan. 30, 2019.

(51) Int. Cl.
| | | |
|---|---|---|
| *G09B 23/28* | (2006.01) | |
| *A61B 8/00* | (2006.01) | |
| *A61B 8/12* | (2006.01) | |

(52) U.S. Cl.
CPC ............ *G09B 23/286* (2013.01); *A61B 8/12* (2013.01); *A61B 8/4263* (2013.01)

(58) Field of Classification Search
CPC ....... G09B 23/28; G09B 23/286; G09B 23/30
See application file for complete search history.

(56) References Cited

U.S. PATENT DOCUMENTS

| | | | |
|---|---|---|---|
| 1,488,233 | A | 3/1924 | Frederick |
| 1,762,937 | A | 6/1930 | Staud |
| 2,019,121 | A | 10/1935 | De Rewal |
| 2,112,019 | A | 3/1938 | Gyger |
| 2,127,610 | A | 8/1938 | Moore |
| 2,705,049 | A | 3/1955 | Brooks |

(Continued)

FOREIGN PATENT DOCUMENTS

| | | |
|---|---|---|
| EP | 1103223 A2 | 5/2001 |
| EP | 2801966 A1 | 11/2014 |

(Continued)

OTHER PUBLICATIONS

Garrido-Jurado et al., Automatic generation and detection of highly reliable fiducial markers under occlusion, 2014, Pattern Recognition.

(Continued)

*Primary Examiner* — Kurt Fernstrom
(74) *Attorney, Agent, or Firm* — Cislo & Thomas, LLP

(57) ABSTRACT

A training system to teach use of an ultrasound probe, the training system having a chamber defining an orifice, a shaft insertable into the orifice of the chamber, a marker positioned on the shaft at a distal end, a camera positioned to view the marker when inserted inside the chamber, and a processor operatively connected to the camera for processing a position and an orientation of the shaft based on the marker. The system provides a method for visualizing movement of the shaft from inside the chamber.

16 Claims, 9 Drawing Sheets

(56) References Cited

U.S. PATENT DOCUMENTS

| | | |
|---|---|---|
| 2,705,307 A | 3/1955 | Nyswander |
| 2,722,947 A | 11/1955 | Sragal |
| 2,886,316 A | 5/1959 | Ayala |
| 4,040,171 A | 8/1977 | Cline et al. |
| 4,838,863 A | 6/1989 | Allard et al. |
| 4,838,869 A | 6/1989 | Allard |
| 4,994,034 A | 2/1991 | Botich et al. |
| 5,231,381 A | 7/1993 | Duwaer |
| 5,513,992 A | 5/1996 | Refait |
| 5,609,485 A | 3/1997 | Bergman et al. |
| 5,678,565 A | 10/1997 | Sarvazyan |
| 5,689,443 A | 11/1997 | Ramanathan |
| 5,701,900 A | 12/1997 | Shehada et al. |
| 5,704,791 A | 1/1998 | Gillio |
| 5,755,577 A | 5/1998 | Gillio |
| 5,767,839 A | 6/1998 | Rosenberg |
| 5,776,062 A | 7/1998 | Nields |
| 5,791,908 A | 8/1998 | Gillio |
| 5,800,177 A | 9/1998 | Gillio |
| 5,800,178 A | 9/1998 | Gillio |
| 5,800,179 A * | 9/1998 | Bailey .................. G09B 23/285 434/262 |
| 5,800,350 A | 9/1998 | Coppleson et al. |
| 5,827,942 A | 10/1998 | Madsen et al. |
| 5,882,206 A | 3/1999 | Gillio |
| 5,889,237 A | 3/1999 | Makinwa |
| 5,934,288 A | 8/1999 | Avila et al. |
| 6,001,472 A | 12/1999 | Ikeda et al. |
| 6,048,312 A | 4/2000 | Ishrak et al. |
| 6,063,030 A | 5/2000 | Vara et al. |
| 6,068,597 A | 5/2000 | Lin |
| 6,074,213 A | 6/2000 | Hon |
| 6,113,395 A | 9/2000 | Hon |
| 6,117,078 A | 9/2000 | Lysyansky et al. |
| 6,119,033 A | 9/2000 | Spigelman et al. |
| 6,122,538 A | 9/2000 | Sliwa, Jr. et al. |
| 6,156,213 A | 12/2000 | Dudley et al. |
| 6,193,657 B1 | 2/2001 | Drapkin |
| 6,267,599 B1 | 7/2001 | Bailey |
| 6,468,212 B1 | 10/2002 | Scott et al. |
| 6,502,756 B1 | 1/2003 | F.ang.hraeus |
| 6,511,427 B1 | 1/2003 | Sliwa, Jr. et al. |
| 6,548,768 B1 | 4/2003 | Pettersson et al. |
| 6,570,104 B1 | 5/2003 | Ericson et al. |
| 6,654,000 B2 | 11/2003 | Rosenberg |
| 6,663,008 B1 | 12/2003 | Pettersson et al. |
| 6,665,554 B1 | 12/2003 | Charles et al. |
| 6,666,376 B1 | 12/2003 | Ericson |
| 6,667,695 B2 | 12/2003 | Pettersson et al. |
| 6,674,427 B1 | 1/2004 | Pettersson et al. |
| 6,689,966 B2 | 2/2004 | Wiebe |
| 6,693,626 B1 | 2/2004 | Rosenberg |
| 6,694,163 B1 | 2/2004 | Vining |
| 6,698,660 B2 | 3/2004 | F.ang.hraeus et al. |
| 6,714,213 B1 | 3/2004 | Lithicum et al. |
| 6,714,901 B1 | 3/2004 | Cotin et al. |
| 6,719,470 B2 | 4/2004 | Berhin |
| 6,722,574 B2 | 4/2004 | Skantze et al. |
| 6,732,927 B2 | 5/2004 | Olsson et al. |
| 6,750,877 B2 | 6/2004 | Rosenberg et al. |
| 6,780,016 B1 | 8/2004 | Toly |
| 6,816,148 B2 | 11/2004 | Mallett et al. |
| 6,836,555 B2 | 12/2004 | Ericson et al. |
| 6,854,821 B2 | 2/2005 | Ericson et al. |
| 6,864,880 B2 | 3/2005 | Hugosson et al. |
| 6,878,062 B2 | 4/2005 | Bjorklund et al. |
| 6,896,650 B2 | 5/2005 | Tracey et al. |
| 6,916,283 B2 | 7/2005 | Tracey et al. |
| 6,927,916 B2 | 8/2005 | Craven-Bartle |
| 6,929,183 B2 | 8/2005 | Pettersson |
| 6,929,481 B1 | 8/2005 | Alexander et al. |
| 6,947,033 B2 | 9/2005 | F.ang.hraeus et al. |
| 6,958,747 B2 | 10/2005 | Sahlberg et al. |
| 6,966,495 B2 | 11/2005 | Lynggaard et al. |
| 6,992,655 B2 | 1/2006 | Ericson et al. |
| 7,002,559 B2 | 2/2006 | Ericson |
| 7,035,429 B2 | 4/2006 | Andreasson |
| 7,037,258 B2 | 5/2006 | Chatenever et al. |
| 7,050,653 B2 | 5/2006 | Edso et al. |
| 7,054,487 B2 | 5/2006 | Ericson et al. |
| 7,072,529 B2 | 7/2006 | Hugosson et al. |
| 7,089,308 B2 | 8/2006 | Fransson et al. |
| 7,094,977 B2 | 8/2006 | Ericson et al. |
| 7,110,604 B2 | 9/2006 | Olsson |
| 7,120,320 B2 | 10/2006 | Petterson et al. |
| 7,121,465 B2 | 10/2006 | Rignell |
| 7,127,682 B2 | 10/2006 | Sandstrom et al. |
| 7,143,952 B2 | 12/2006 | Ericson |
| 7,145,556 B2 | 12/2006 | Pettersson |
| 7,154,056 B2 | 12/2006 | Bergqvist et al. |
| 7,162,087 B2 | 1/2007 | Bryborn |
| 7,167,164 B2 | 1/2007 | Ericson et al. |
| 7,172,131 B2 | 2/2007 | Pettersson et al. |
| 7,175,095 B2 | 2/2007 | Pettersson et al. |
| 7,176,896 B1 | 2/2007 | Fahraeus et al. |
| 7,180,509 B2 | 2/2007 | Fermgard et al. |
| 7,195,166 B2 | 3/2007 | Olsson et al. |
| 7,202,861 B2 | 4/2007 | Lynggaard |
| 7,202,963 B2 | 4/2007 | Wiebe et al. |
| 7,239,306 B2 | 7/2007 | Fahraeus et al. |
| 7,246,321 B2 | 7/2007 | Bryborn et al. |
| 7,248,250 B2 | 7/2007 | Pettersson et al. |
| 7,249,256 B2 | 7/2007 | Hansen et al. |
| 7,249,716 B2 | 7/2007 | Bryborn |
| 7,254,839 B2 | 8/2007 | Fahraeus et al. |
| 7,278,017 B2 | 10/2007 | Skantze |
| 7,281,668 B2 | 10/2007 | Pettersson et al. |
| 7,283,676 B2 | 10/2007 | Olsson |
| 7,293,697 B2 | 11/2007 | Wiebe et al. |
| 7,295,193 B2 | 11/2007 | Fahraeus |
| 7,296,075 B2 | 11/2007 | Lynggaard |
| 7,321,692 B2 | 1/2008 | Bryborn et al. |
| 7,333,947 B2 | 2/2008 | Wiebe et al. |
| 7,345,673 B2 | 3/2008 | Ericson et al. |
| 7,353,393 B2 | 4/2008 | Hansen et al. |
| 7,356,012 B2 | 4/2008 | Wiebe et al. |
| 7,371,068 B2 | 5/2008 | Lloyd et al. |
| 7,382,361 B2 | 6/2008 | Burstrom et al. |
| 7,385,595 B2 | 6/2008 | Bryborn et al. |
| 7,408,536 B2 | 8/2008 | Hugosson et al. |
| 7,415,501 B2 | 8/2008 | Burstrom |
| 7,418,160 B2 | 8/2008 | Lynggaard |
| 7,422,154 B2 | 9/2008 | Ericson |
| 7,441,183 B2 | 10/2008 | Burstrom et al. |
| 7,457,413 B2 | 11/2008 | Thuvesholmen et al. |
| 7,457,476 B2 | 11/2008 | Olsson |
| 7,543,753 B2 | 6/2009 | Pettersson |
| 7,588,191 B2 | 9/2009 | Pettersson et al. |
| 7,600,693 B2 | 10/2009 | Pettersson |
| 7,649,637 B2 | 1/2010 | Wiebe et al. |
| 7,670,070 B2 | 3/2010 | Craven-Bartle |
| 7,672,513 B2 | 3/2010 | Bjorklund et al. |
| 7,701,446 B2 | 4/2010 | Sahlberg et al. |
| 7,710,408 B2 | 5/2010 | Ericson |
| 7,751,089 B2 | 7/2010 | Fahraeus et al. |
| 7,753,283 B2 | 7/2010 | Lynggaard |
| 7,777,777 B2 | 8/2010 | Bowman et al. |
| 7,788,315 B2 | 8/2010 | Johansson |
| 7,794,388 B2 | 9/2010 | Draxinger et al. |
| 7,806,696 B2 | 10/2010 | Alexander et al. |
| 7,833,018 B2 | 11/2010 | Alexander et al. |
| 7,845,560 B2 | 12/2010 | Emanuel et al. |
| 7,850,454 B2 | 12/2010 | Toly |
| 7,857,626 B2 | 12/2010 | Toly |
| 7,871,850 B2 | 1/2011 | Park |
| 7,931,470 B2 | 4/2011 | Alexander et al. |
| 8,116,549 B2 | 2/2012 | Warmath et al. |
| 8,244,506 B2 | 8/2012 | Butsev et al. |
| 8,294,972 B2 | 10/2012 | Chung |
| 8,428,326 B2 | 4/2013 | Falk et al. |
| 8,480,404 B2 | 7/2013 | Savitsky |
| 8,480,406 B2 | 7/2013 | Alexander et al. |
| 8,721,344 B2 | 5/2014 | Marmaropoulos et al. |
| 9,128,116 B2 | 9/2015 | Welch et al. |

(56) References Cited

U.S. PATENT DOCUMENTS

| | | | |
|---|---|---|---|
| 9,171,484 B2 | 10/2015 | Fitzli et al. | |
| 9,251,721 B2* | 2/2016 | Lampotang | G09B 9/00 |
| 9,436,993 B1 | 9/2016 | Stolka et al. | |
| 9,626,805 B2 | 4/2017 | Lampotang et al. | |
| 9,792,836 B2 | 10/2017 | Rios et al. | |
| 9,870,721 B2 | 1/2018 | Savitsky et al. | |
| 9,918,657 B2 | 3/2018 | Daon et al. | |
| 10,052,010 B2 | 8/2018 | Feddema | |
| 10,132,015 B2 | 11/2018 | Woodruff et al. | |
| 11,011,077 B2* | 5/2021 | Garcia Kilroy | A61B 34/10 |
| 2001/0031920 A1 | 10/2001 | Kaufman et al. | |
| 2002/0076581 A1 | 6/2002 | McCoy | |
| 2002/0076681 A1 | 6/2002 | Leight et al. | |
| 2002/0088926 A1 | 7/2002 | Prasser | |
| 2002/0099310 A1 | 7/2002 | Kimchy et al. | |
| 2002/0168618 A1 | 11/2002 | Anderson et al. | |
| 2002/0173721 A1 | 11/2002 | Grunwald et al. | |
| 2003/0210812 A1 | 11/2003 | Khamene et al. | |
| 2004/0043368 A1 | 3/2004 | Hsieh et al. | |
| 2004/0087850 A1 | 5/2004 | Okerlund et al. | |
| 2005/0084833 A1 | 4/2005 | Lacey et al. | |
| 2005/0119569 A1 | 6/2005 | Ohtake | |
| 2005/0181342 A1* | 8/2005 | Toly | G09B 23/30 |
| | | | 434/262 |
| 2005/0214726 A1 | 9/2005 | Feygin et al. | |
| 2005/0228617 A1 | 10/2005 | Kerwin et al. | |
| 2005/0283075 A1 | 12/2005 | Ma et al. | |
| 2006/0020204 A1 | 1/2006 | Serra et al. | |
| 2006/0098010 A1 | 5/2006 | Dwyer et al. | |
| 2007/0088213 A1 | 4/2007 | Poland | |
| 2007/0161904 A1 | 7/2007 | Urbano | |
| 2007/0232907 A1 | 10/2007 | Pelissier et al. | |
| 2007/0233085 A1 | 10/2007 | Colvin et al. | |
| 2007/0236514 A1* | 10/2007 | Agusanto | G02B 27/0093 |
| | | | 345/646 |
| 2008/0009743 A1 | 1/2008 | Hayasaka | |
| 2008/0137071 A1 | 6/2008 | Chow | |
| 2008/0187896 A1 | 8/2008 | Savitsky | |
| 2008/0200807 A1 | 8/2008 | Wright et al. | |
| 2008/0204004 A1 | 8/2008 | Anderson | |
| 2008/0269606 A1 | 10/2008 | Matsumura | |
| 2008/0294096 A1 | 11/2008 | Uber et al. | |
| 2008/0312884 A1 | 12/2008 | Hostettler et al. | |
| 2009/0043195 A1 | 2/2009 | Poland | |
| 2009/0046912 A1 | 2/2009 | Hostettler | |
| 2009/0130642 A1 | 5/2009 | Tada et al. | |
| 2009/0209859 A1 | 8/2009 | Tsujita et al. | |
| 2009/0266957 A1 | 10/2009 | Cermak | |
| 2009/0305213 A1 | 12/2009 | Burgkart et al. | |
| 2009/0311655 A1 | 12/2009 | Karkanias et al. | |
| 2010/0055657 A1 | 3/2010 | Goble et al. | |
| 2010/0104162 A1 | 4/2010 | Falk et al. | |
| 2010/0179428 A1 | 7/2010 | Pedersen et al. | |
| 2010/0268067 A1 | 10/2010 | Razzaque et al. | |
| 2010/0277422 A1 | 11/2010 | Muresianu et al. | |
| 2011/0010023 A1 | 1/2011 | Kunzig et al. | |
| 2011/0306025 A1 | 12/2011 | Sheehan et al. | |
| 2012/0021993 A1 | 1/2012 | Kim et al. | |
| 2012/0143142 A1 | 6/2012 | Klein | |
| 2012/0150797 A1 | 6/2012 | Landy et al. | |
| 2012/0179039 A1 | 7/2012 | Pelissier et al. | |
| 2012/0200977 A1 | 8/2012 | Nestler | |
| 2012/0219937 A1 | 8/2012 | Hughes et al. | |
| 2012/0238875 A1 | 9/2012 | Savitsky et al. | |
| 2012/0251991 A1 | 10/2012 | Savitsky et al. | |
| 2013/0046523 A1* | 2/2013 | Van Dinther | G09B 9/00 |
| | | | 703/6 |
| 2013/0064036 A1 | 3/2013 | Lee et al. | |
| 2013/0065211 A1 | 3/2013 | Amso et al. | |
| 2013/0158411 A1 | 6/2013 | Miyasaka | |
| 2013/0179306 A1 | 7/2013 | Want et al. | |
| 2013/0236872 A1 | 9/2013 | Laurusonis et al. | |
| 2013/0267838 A1 | 10/2013 | Fronk et al. | |
| 2014/0087347 A1* | 3/2014 | Tracy | G09B 23/285 |
| | | | 434/272 |
| 2014/0114194 A1 | 4/2014 | Kanayama et al. | |
| 2014/0120505 A1 | 5/2014 | Rios et al. | |
| 2014/0228685 A1 | 8/2014 | Eelbode | |
| 2014/0272878 A1 | 9/2014 | Shim et al. | |
| 2015/0056591 A1 | 2/2015 | Tepper et al. | |
| 2015/0073639 A1 | 3/2015 | Hausotte | |
| 2015/0086955 A1 | 3/2015 | Poniatowski et al. | |
| 2015/0190112 A1 | 7/2015 | Yeo et al. | |
| 2015/0213731 A1* | 7/2015 | Sato | G09B 23/288 |
| | | | 434/272 |
| 2016/0104393 A1 | 4/2016 | Savitsky et al. | |
| 2016/0133158 A1 | 5/2016 | Sui et al. | |
| 2016/0284240 A1 | 9/2016 | Liang | |
| 2016/0314716 A1* | 10/2016 | Grubbs | G09B 23/306 |
| 2016/0328998 A1 | 11/2016 | Pedersen et al. | |
| 2017/0028141 A1 | 2/2017 | Fiedler et al. | |
| 2017/0035517 A1* | 2/2017 | Geri | A61B 34/20 |
| 2017/0046985 A1 | 2/2017 | Hendrickson et al. | |
| 2017/0110032 A1* | 4/2017 | O'Brien | A61B 8/483 |
| 2017/0200399 A1 | 7/2017 | Thomas et al. | |
| 2017/0270829 A1 | 9/2017 | Bauss | |
| 2017/0352295 A1 | 12/2017 | Belzacq et al. | |
| 2017/0372640 A1 | 12/2017 | Lampotang et al. | |
| 2018/0049622 A1 | 2/2018 | Ryan et al. | |
| 2018/0071032 A1 | 3/2018 | de Almeida Barreto | |
| 2018/0197441 A1* | 7/2018 | Rios | G09B 23/285 |
| 2018/0225992 A1 | 8/2018 | Gonsalves | |
| 2018/0366034 A1* | 12/2018 | Casals Gelpí | G09B 23/285 |
| 2019/0057620 A1* | 2/2019 | Eggert | G09B 5/14 |
| 2019/0231436 A1* | 8/2019 | Panse | A61B 34/20 |
| 2019/0321657 A1 | 10/2019 | Hale | |
| 2020/0126449 A1* | 4/2020 | Horst | G09B 23/285 |
| 2020/0138518 A1 | 5/2020 | Lang | |
| 2021/0128125 A1 | 5/2021 | Sitti et al. | |
| 2021/0186311 A1 | 6/2021 | Levy et al. | |

FOREIGN PATENT DOCUMENTS

| | | |
|---|---|---|
| RU | 2127610 C1 | 3/1999 |
| RU | 1994040171 | 11/2014 |
| WO | 2006060406 A1 | 6/2006 |
| WO | WO 2009/003664 | 1/2009 |
| WO | WO 2013/140315 | 9/2013 |
| WO | PCT/US2013/058661 | 3/2014 |
| WO | WO 2017/098036 | 6/2017 |

OTHER PUBLICATIONS

Healthcare Solutions, 3D Systems, Pelvic Mentor, 3 pages.
Sonocubic Fine, "A Revolution in Obstetrical Ultrasound," 1 page.
Medge Platforms, Inc., "Volutracer O.P.U.S. Optical Positioning Ultrasound Simulator," 2 pages.
Chung, Gregory, "Effects of Simulation-Based Practice on Focused Assessment . . . ", Military Medicine, Oct. 2013, vol. 178.
Aligned Management Associates, Inc., Corporate home page describing organizing committee, overview, Procedicus MiST[trademark]-suturing module 30.0, 6 pgs., obtained from website Sep. 6, 2004.
American Academy of Emergency Medicine, conference: 11th annual scientific assembly preconference ultrasound courts, http://www.aaem.org/education/scientificassembiy/sa05/precon/ultrasound.shtmi, 6 pgs, obtained from website Feb. 16, 2005.
Barbosa, J. et al., "Computer education in emergency medicine residency programs," http://www.med-ed-online.org/res00002.htm, 8 pgs, obtained from website Sep. 6, 2004.
Brannam, Let al, "Emergency nurses utilization of ultrasound guidance for placement of peripheral intravenous lines in difficult-access patients," Acad Emerg Med, 11(12):1361-1363, Dec. 2004.
Calvert, N. et al., "The effectiveness and cost-effectiveness of ultrasound locating devices for central venous access: a systematic review and economic evaiuation/executive summary," Health Tech Assess 2003, 7(12), 4 pgs.
Center for Human Simulation, corporate home page describing overview/people, http://www.uchsc.edu, 7 pgs, obtained from website Sep. 6, 2004.
CIMIT News, "The medical access program: new CIMIT initiative to benefit underserved patients/partners telemedicine and CIMIT

(56) References Cited

OTHER PUBLICATIONS launch new initiative: stay connected, be healthy/highlights: operating room of the future plug-and-play project," http://www.cimit.org, Jan. 2005; Volll(2), 2 pgs., obtained from website Mar. 1, 2005.
Colt, H. G. et al., "Virtual reality bronchoscopy simulation: a revolution in procedural training," Chest 2001; 120:1333-1339.
Computer Motion, "About computer motion: technology to enhance surgeons capabilities, improve patient outcomes and reduce healthcare costs/corporate alliances/products solutions for surgical innovation/ training on the da Vinci[registered] surgical system-introduction," 2002 Computer Motion, http://www.computermotion.com, 6 pgs.
Delp, Setai, "Surgical simulation—an emerging technology fortraining in emergency medicine," Presence, 6 (2):147-159, Apr. 1997 (abstract).
Dorner, R. et. al., "Synergies between interactive training simulations and digital storytelling: a component-based framework," Computer Graphics, 26(1):45-55, Feb. 2002 (abstract).
Duque, D. and Kessler S., "Ultrasound guided vascular access," Amer Coli Emerg Phy., http://vww.nyacep.org/education/articles/ultrasound%20vascular%20access.htm, 2 pgs, obtained from website May 11, 2005.
Espinet, A. and Dunning J., "Does ultrasound-guided central line insertion reduce complications and time to placement in elective patients undergoing cardiac surgery," Inter Cardiovascular Thoracic Surg, 3:523-527, 2004; http:/licvts.ctsnetjournals.org/cgi/content/full/3/3/523, 6 pgs, obtained from website May 11, 2005 (abstract).
Gallagher, A. G. et al., "Virtual reality training for the operating room and cardiac catheterization laboratory," Lancet, 364:1538-1540, Oct. 23, 2004.
Gallagher, A. G. et al., "Psychomotor skills assessment in practicing surgeons experienced in performing advanced laparoscopic procedures," AM Coli Surg, 197(3):479-488, Sep. 2003.
Gausche, M. et al., "Effect on out-of-hospital pediatric endotracheal Intubation on survival and neurological outcome: a controlled clinical trial," JAMA, 283(6)783-790, Feb. 9, 2000.
Gore, D. C. and Gregory, S. R., "Historical perspective on medical errors: Richard Cabot and the Institute of Medicine," J Amer Coli Surg, 197(4), 5 pgs, Oct. 2003.
Grantcharov, T. P. et al., "Randomized clinical trial of virtual reality simulation for laparoscopic skills training," Br J Surg, 91 (2):146-150, Feb. 1, 2004 (abstract).
Grantcharov, T. P. et al., "Learning curves and impact of previous operative experience on performance on a virtual reality simulator to test laparoscopic surgical skills," Am J Surg, 185(2):146-149, Feb. 1, 2004 (abstract).
Haluck, R. S., et al., "Are surgery training programs ready for virtual reality A survey of program directors in general surgery," Arch Surg, 135(7):786-792, Jul. 1, 2000.
Helmreich, R. L., "On error management: lessons from aviation," BMJ, 320:781-785, Mar. 2000.
Huckman, R. S. and Pisano, G. P., "Turf battles in coronary revascularization," N Engl J Med, http://www.nejm.org, 4 pgs. 352(9):857-859, Mar. 3, 2005.
Immersion Corporation, URL: http://www.immersion.com/corporate/products/, corporate home page describing Immersions surgical training simulators—"Wireless Data Glove: The CyberGiove[registered]II System," 5 pgs, obtained from the website Nov. 17, 2005 and Jan. 24, 2008.
Injuryboard.com, "Reducing complications associated with central vein catheterization," URSL: http://www.injuryboard.com/view.cfm/Article=668, 5 pgs, obtained from website May 11, 2005.
INTERSENSE, home page listing motion tracking products, http://www.isense.com/prodcuts.aspxid=42,1 pg, obtained from website Jan. 24, 2008.

Jemmett, M. E., et. al., "Unrecognized misplacement of endotracheal tubes in a mixed urban to rural emergency medical services setting," Acad Emerg Med, 10(9):961-964, Sep. 2003.
Katz, S. H. and Falk, J. L., "Misplaced endotrachial tubes by paramedics in an urban medical services system," Annals Emerg Med, 37:32-37, Jan. 2001.
Lewis, R., "Educational research: time to reach the bar, not lower it," Acad Emerg Med, 12(3):247-248, Mar. 2005.
Liu, A. et, al., "A survey of surgical simulation: applications, technology, and education," Presence, 12(6):1-45, Dec. 2003.
Manchester Visulations Centre, "Webset project-bringing 3D medical training tools to the WWW," http://www.sve.man.ac.uklmvc/research/previous/website, 3 pgs, obtained from the website Sep. 8, 2004.
Mclellan, H., "Virtual realities," Mclellan Wyatt Digital, 33 pgs.
Medical Simulation Corporation, corporate home page describing management team/frequently asked questions, http://www.medsimulation.com/about_msc/key_employees.asp, 7 pgs, obtained from website Nov. 25, 2004.
Medtronic, "The StealthStation[registered] treatment guidance system," the corporate home page describing the company fact sheet and profile; http://www.medtronic.com/Newsroom, 4 pgs, obtained from website Mar. 5, 2005.
Mort, T. C., "Emergency tracheal intubation: complications associated with repeated laryngoscopic attempts," Anesth Analg, 99(2):607-613, Aug. 2004, 1 pg, obtained from website Sept. 8, 2004 (abstract).
Nazeer, S. R., et al., "Ultrasound-assisted paracentesis performed by emergency physicians v.s. the traditional technique: a prospective, randomized study," Amer J of Emer Med, 23:363-367, 2005.
NCA Medical Simulation Center, Tutorial-simulation for medical training, http://Simcen.usuhs.milimiccaie, 4 pgs, 2003.
Next Dimension Imaging, "Products-Anatomy Analyzer 2," http://www.nexted.com/anatomyanalyzer.asp, 2 pgs, obtained from website Dec. 7, 2004.
Norris, T. E. et al., "Teaching procedural skills," J General Internal Med, 12(S2):S64-S70, Apr. 1997.
On the Net Resources-Education and Training, URL: http://www.hitl.washington.edu/projects/knowledge_base/education.html, corporate home page regarding internet sites regarding education and training, 16 pgs, obtained from website Jan, 8, 2005.
Osberg, K. M., "Virtual reality and education: a look at both sides of the sword," http://www.hitl.washington.edu/pubiications/r-93-7/, 19 pgs, Dec. 14, 1992, obtained from website Jan. 21, 2008.
Osmon, S. et al., "Clinical investigations: reporting of medical errors: an intensive care unit experience," Grit Care Med. 32(3), 13 pgs, Mar. 2004.
Ponder, M., et al., "Immersive VR decision training: telling Interactive stories featuring advanced human simulation technologies," Eurographics Association 2003, 10 pgs.
Primal, corporate home page describing resources forteaching healthcare practitioners, 2 pgs, obtained from website.
Prystowsky, J. B. et al., "A virtual reality module for intravenous catheter placement," Am J Surg 1999; 177 (2):171-175 (abstract).
Reachin, "Medical Training Development Centre/Reachin technologies AB has entered into a corporation with Mentice AB," Jan. 20, 2004, 4 pgs, obtained from website Nov. 9, 2004.
Rothschild, J. M., "Ultrasound guidance of central vein catheterization," NCBI, Nat Lib Med, www.ncbi.nlm.nih.gov/books/, HSTAT 21,6 pgs, obtained from website May 11, 2005.
Rowe, R. and Cohen, R. A., "An evaluation of a virtual reality airway simulator," Anesth Analg 2002, 95:62-66.
Sensable Technologies, "PHANTOM Omni Haptic Device," 2 pgs, http://www.sensable.com/haptic-ohantom-omni.htm., obtained from website Jan. 24, 2008.
Shaffer, K., "Becoming a physician: teaching anatomy in a digital age," NEJM, Sep. 23, 2004; 351(13):1279-81 (extract of first 100 words—no abstract).

\* cited by examiner

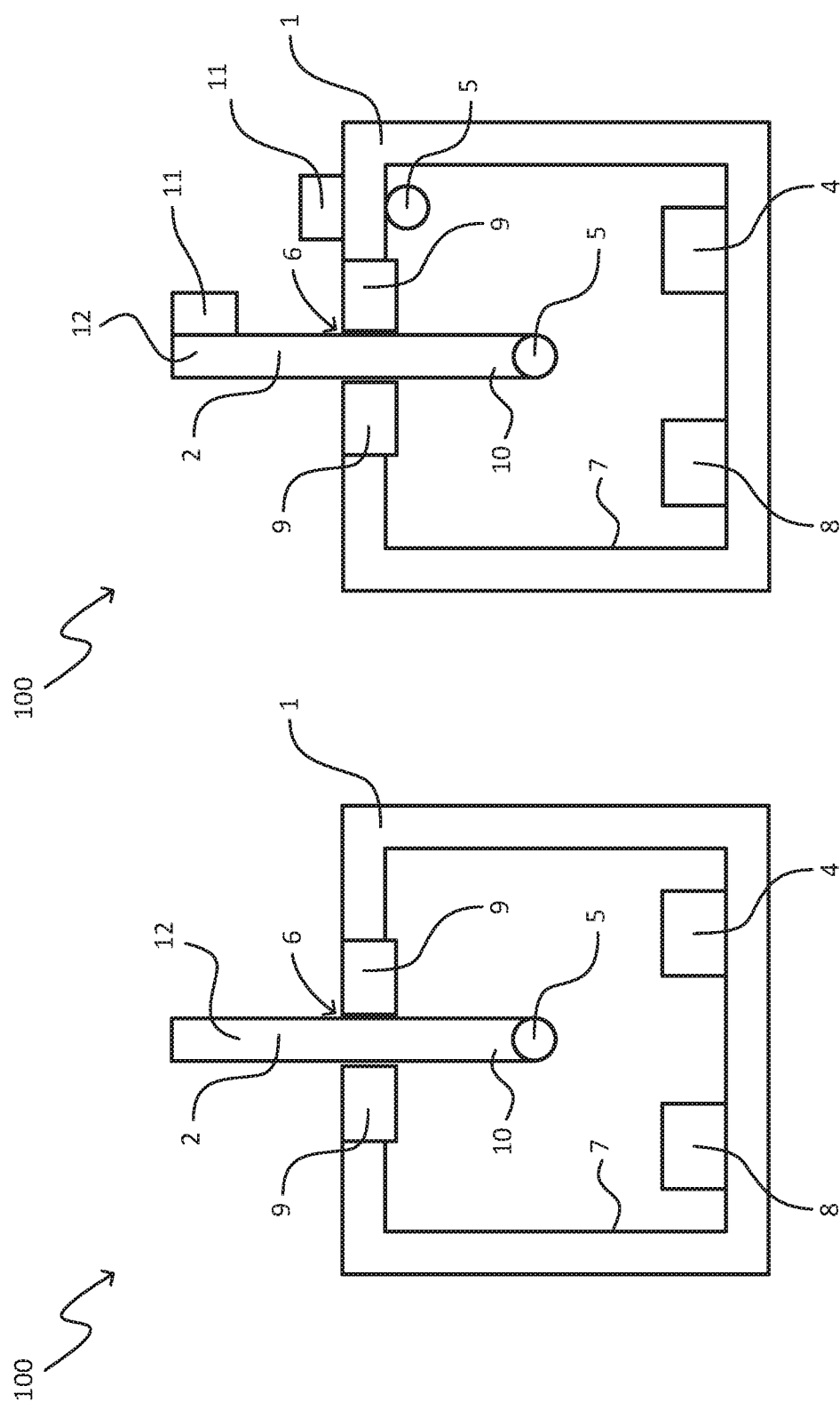

ULTRASOUND TRAINER WITH INTERNAL OPTICAL TRACKING

CROSS-REFERENCE TO RELATED APPLICATION

This patent application claims the benefit of U.S. Provisional Patent Application Ser. No. 62/798,860, entitled "Ultrasound Trainer with Internal Optical Tracking," filed Jan. 30, 2019, which application is incorporated in its entirety here by this reference.

BACKGROUND

Currently available ultrasound simulation solutions that deliver endolumenal ultrasound simulation utilize excessively complex, large physical footprint, and expensive inertial tracking, or alternative motion sensing, technologies. The latter motion-sensing options are not compatible with individual user utilization due to practical (e.g., large form factor) and cost considerations, thereby—limiting ultrasound training options. The proposed invention would deliver 6-DOF simulated endolumenal ultrasound probe movement using a compact form factor for a scalable individual user training solution.

SUMMARY

The present invention is directed towards a training system to teach use of a medical device, such as an ultrasound probe. The training system comprises a chamber defining an orifice; a shaft insertable into the orifice of the chamber, the shaft having a proximal end and a distal end; a marker positioned on the shaft at the distal end; a camera positioned to view the marker when inserted inside the chamber; and a processor operatively connected to the camera for processing a position and an orientation of the shaft based on the marker.

In some embodiments, the system may further comprise a motion limiter connected to the chamber at the orifice.

In some embodiments, the system may further comprise a light source to illuminate the chamber.

In some embodiments, the chamber mimics a body or a body part.

BRIEF DESCRIPTION OF DRAWINGS

FIG. 1 is a schematic diagram of an embodiment of the present invention.

FIG. 2 is a schematic diagram of an embodiment of the present invention.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The invention of the present application is a training system 100 for the mastery of ultrasound procedures, including, but not limited to endolumenal (or endoluminal) ultrasound procedures, also known as endoscopic ultrasound (EUS) medical procedures, transvaginal sonography (TVS) or OB-GYN ultrasonography, rectal endoscopic sonography (RES), transesophageal echocardiogram (TEE), endobronchial, intestinal, intravascular ultrasound (IVUS) or similar diagnostic techniques where an imaging probe is inserted into a bodily lumen of a human or animal subject.

Figure 3:
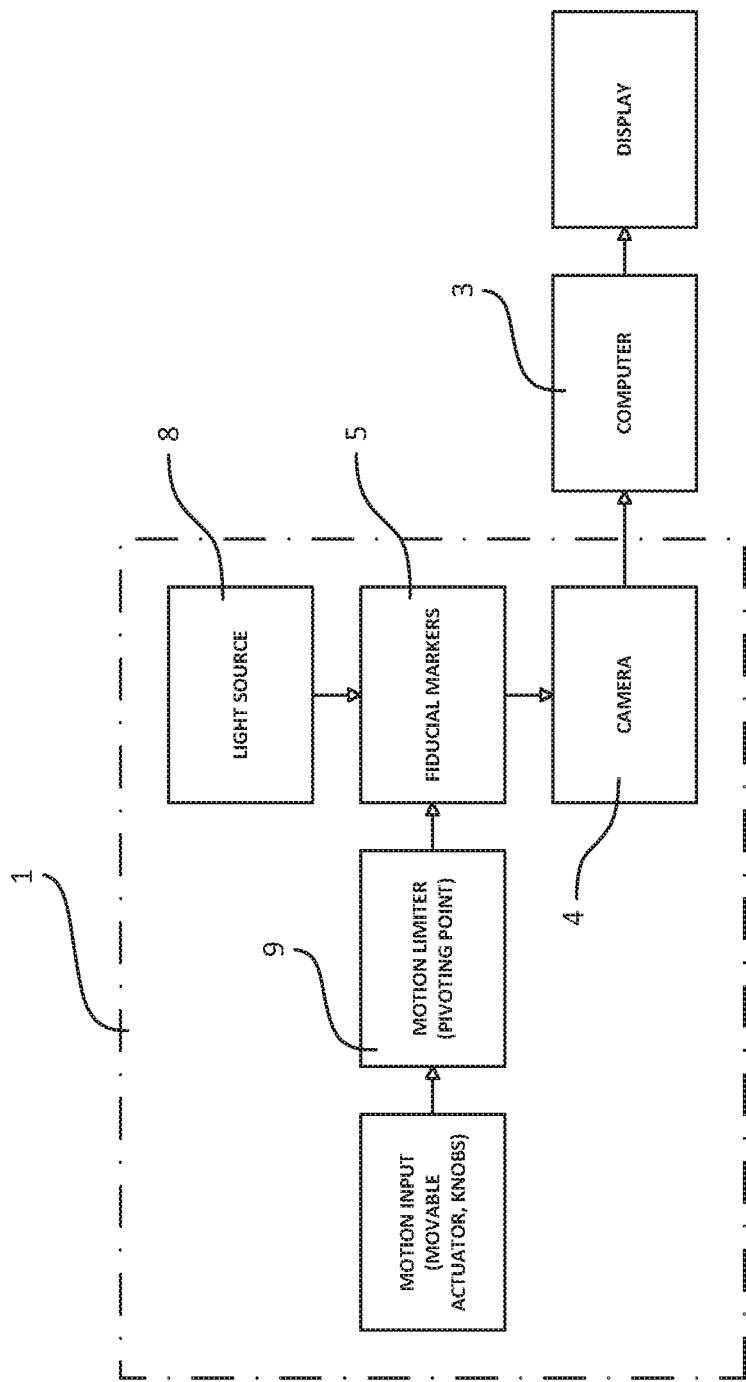
FIG. 3 is a flow diagram of an embodiment of the present invention.

With reference to FIGS. 1-3, in the preferred embodiment, the training system 100 comprises: a chamber 1 defining an orifice 6, a shaft 2 insertable into the chamber 1 through the orifice 6, a marker 5 on the shaft 2, a camera 4 configured to view inside the chamber 1 towards the orifice 6, and a processor 3 operatively connected to the camera 4 to process information. In some embodiments, a motion limiter 9 can be attached to the chamber 1 at the orifice 6. In some embodiments, a light source 8 can be configured to illuminate inside the chamber 1.

The marker 5 is an indicium endowed with a distinctive appearance and a known geometric structure (shape) that can be detected by the camera 4. For example, the indicium may be a printed pattern or other marking applied to shaft 2. The marker 5 can be affixed rigidly to one end of shaft 2 by way of an adhesive, other bonding solution, or any other type of fastener, or may be printed directly on the surface of shaft 2. In some embodiments, the marker 5 may be formed directly into shaft 2 either during the manufacturing process of the shaft 2 or as a post-production modification.

The shaft 2 itself may be constructed of a rigid material or a flexible material, as long as the flexure of the shaft 2 does not cause significant distortion of the appearance of the marker 5. The shaft 2 has a handle 12 and a distal end 10 opposite the handle 12 to mimic typical imaging probes, such as ultrasound probes. The distal end 10 of shaft 2 bears the marker 5. As such, the distal end 10 is insertable into the chamber 1 through the orifice 6. The distal end 10 of shaft 2 where the marker 5 is located may be referred to as the "tip" of shaft 2. Shaft 2 emulates an imaging probe being inserted into a bodily lumen. The tip of shaft 2 emulates the location of the detector or transducer in a real endolumenal imaging probe, such as a transvaginal ultrasound probe, a transesophageal ultrasound probe, or an intravascular ultrasound probe. In order to increase the realism of the endoluminal ultrasound trainer, the preferred embodiment molds the shaft 2 to resemble a particular type of endolumenal ultrasound probe, and the outside of the chamber 1 to resemble a section of the human body or the body of an animal. One may also choose to affix an marker 5 to a real clinical probe, while ensuring that the appearance of the probe, which may be made of a reflective type of material, does not disturb the view of the optical marker 5 by the camera 4, introducing glare and other undesirable optical artifacts.

Figure 4:
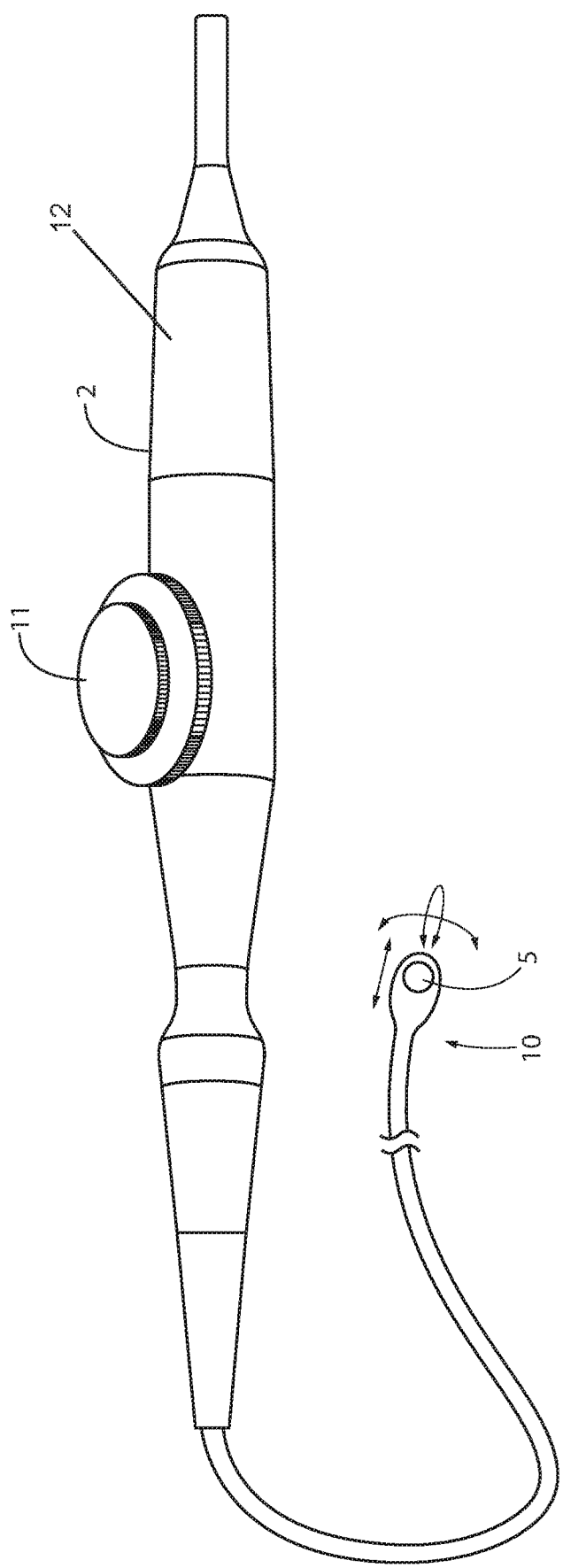
FIG. 4 is a perspective view of an embodiment of the present invention.

In some embodiments, shaft 2 may have a tip 10 that can be bent, through flexing or articulation, independently from the main shaft 2 as shown in FIG. 4. Marker 5 may be applied to the tip 10. The shaft 2 may have one or more controllers 11 on its exterior to mechanically alter the position or orientation of the steerable tip (and thus marker 5 affixed on it). Common controllers 11 known to those skilled in the art may include knobs, joysticks, dials, push buttons, capacitive buttons or any other tactile or electronic control system. The motion of the controller 11 may be transmitted directly to the tip 10 by an intermediate mechanical component or the tactile control may send a signal to a separate actuator to steer the tip 10 in response to the operator's input. Alternatively, the controller 11 may be part of the user interface of an external device, which in turn will send a signal to the shaft 2 and actuate the tip 10. The controller 11 may also be virtual elements of a graphical user interface (GUI) displayed on a screen that may be part of the shaft 2 itself or part of an external computing device.

In some embodiments, at least one marker 5 may be placed on a rigid section of shaft 2 upstream of the tip 10 (i.e., towards the handle), and at least one other marker 5 may be placed on the tip 10. An algorithm can analyze independent observations of each marker 5 and compute the position and orientation of tip 10 and the rigid section of shaft 2 separately.

In some embodiments, if the controller 11 can transmit its state to the processor 3, one can simulate the presence of a tip 10 with a single rigid tubular shaft 2 with one or more markers 5, but without requiring the additional complexity of a mechanically steerable tip. In the latter, the processor 3 computes the location of the imagined steerable extension by combining information from optical tracking and the state of the controllers 11 without requiring a physical mechanism to articulate the tip 10 of the shaft 2.

The chamber 1 is hollow with at least one inner wall 7 defining an interior space. For example, a single curved wall 7 can be used to create a cylindrical or spherical shape, multiple flat walls 7 can be used to create sidewalls, ceilings, and floors, or a combination of curved and flat walls can be used to create other three-dimensional cavities. The inner wall 7 should be constructed with an opaque material that limits the transmission of external light into chamber 1. Preferably, the inside of chamber 1 is constructed of a material that is matte in appearance or alternatively is coated with a substance that reduces its optical reflectivity. Preferably, the distal end 10 of shaft 2 that goes inside chamber 1 should have an appearance that is matte and distinct in color and texture from the appearance of marker 5 so as to create a detectable contrast. Chamber 1 may mimic various body parts, such as the lower body (see, FIGS. 5-10 and 12) such as the vaginal area and rectal area, the head and neck (see, FIG. 11), and the like, where physicians are likely to probe with an imaging probe. In some embodiments, the chamber 1 may be a full-sized manikin commonly used for medical training.

In some embodiments, a motion limiter 9 is formed or attached to the chamber 1 at the orifice 6 and spans its circumference adding thickness to its outer edge. The motion limiter 9 is positioned in such way as to exert mechanical resistance against shaft 2, thus constraining its freedom of motion when the shaft 2 is inserted into chamber 1 and manipulated by the user. Portions of shaft 2 in between the distal end 10 and the handle 12 may be configured to mate with a motion limiter 9, which mechanically constrains shaft 2 to a desired range of motion. The motion limiter 9 may have a flexible rubber trim whose thickness is such to provide tight contact with shaft 2 and limit its insertion via friction and its lateral motion by means of its stiffness against deformation. In this embodiment the contact between the motion limiter 9 and the shaft 2 should be tight enough, so that the user cannot change orientation of the shaft 2 without deforming the shape of motion limiter 9. Therefore, in this embodiment there is a direct correlation between the elasticity (the ability to deform) and coefficient of friction of the motion limiter 9 and the haptics of the shaft 2. Alternatively, the motion limiter 9 may be a cone or other revolved surface of a rigid or semi-rigid material whose profile is calculated appropriately so as to constrain the lateral motion of shaft 2 within a desired solid angle.

The camera 4 faces inside the opaque chamber 1 in such a way that it maintains a clear view of the marker 5 for the entire range of motion of shaft 2 when inserted into the chamber 1. In some embodiments, the camera 4 may be inside the chamber 1. If a single camera 4 cannot observe the marker 5 for the entire range of motion of the shaft 2, the system can employ multiple cameras 4 without violating the spirit of the invention. In some embodiments, the shaft 2 can have multiple distinct markers 5 to ensure that at least one of the markers 5 is always visible by at least one of the cameras 4 for the entire range of motion of the shaft 2. Therefore, each marker 5 may be distinct from another marker 5. In some embodiments, a marker 5 may be on the chamber wall 7, which can serve as a reference point to determine movement of the marker 5 on the shaft 2.

The camera 4 may be operatively connected to a processor that analyzes the visual information captured by the camera 4. The connection may be established with a wired or wireless connection using either a standard protocol, such as USB, Thunderbolt, Bluetooth or Wi-Fi, or a custom protocol as is well known to those skilled in the art. The processor may be a microcontroller placed inside the chamber 1, it may be placed outside the chamber 1 at a remote location, or it may be part of a more complex computing device.

We refer to the combination of the frame data from the camera 4 and the algorithm that runs on the processor as "optical tracking".

The optical tracking described in this invention allows for full 6 degrees-of-freedom (6-DOF) tracking (rotation in 3 spatial dimensions and position in 3 spatial dimensions) of the shaft 2. However, a designer may employ different types of motion limiters 9 to further constrain the motion to, for example, rotation only (3-DOF), rotation and planar motion (5-DOF), rotation and penetration (4-DOF), roll rotation and penetration (2-DOF).

The camera 4 may operate in the visible spectrum or the infrared spectrum, and may support multiple colors or be monochromatic. One skilled in the art understands that the appearance of the marker 5, the opacity of the chamber 1, and the internal coating of the chamber 1 must be chosen in a way that conforms to the chosen spectrum of light. Furthermore, for the purpose of this invention, optical tracking can be achieved adequately if the optical assembly of the camera 4 has a fixed focus, manually adjustable focus, electronically adjustable focus, or auto-focus, or any other variants of varifocal lenses that can resolve the pattern on the marker 5 with sufficient visual acuity. The image sensor of camera 4 can either employ rolling shutter or global shutter.

In some embodiments, the camera 4 may be able to measure depth (e.g., RGBD camera) directly by way of stereo vision, time-of-flight imaging, structured light, or other operating principle known to those skilled in the art. Alternatively, the camera 4 may be a device specifically designed to track the three-dimensional position and orientation of an elongated object such as the commercially available LEAP Motion controller. This embodiment enables applications where the shaft 2 can be an arbitrary elongated object and does not necessarily require modification by affixing a marker 5 to it.

In some embodiments, a light source 8 may also be directed towards the inside of the hollow chamber 1. For example, a light source 8 may be mounted on a mechanical assembly of the camera, or mounted on one of the walls 7 of the chamber 1, or embedded into or attached behind the walls 7 for backlighting. The light source 8 is designed to provide controlled illumination of the marker 5 for the entire range of motion of the shaft 2. In some cases, the designer may employ more than a single light source 8 to ensure uniform illumination of the marker 5 and/or elimination of shadows for the entire range of motion of shaft 2.

In the preferred embodiment, the system may be combined with an external computing device 3 that runs a software ultrasound simulator similar, but not limited, to The SonoSim® Ultrasound Training Solution. An ultrasound simulator comprises at least a case library that contains one or more medical cases of interest, a user interface, a variable image that resembles the appearance of an ultrasound image or other clinical imaging modality, and optionally a virtual representation of a patient along with a visualization of the imaging device being inserted in a bodily lumen. The system described in this invention is connected by means of a wire or wirelessly to a computing device 3 that runs the ultrasound simulator. The computing device 3 may either receive raw frame data directly from the camera 4 and run the algorithm to compute the position and orientation of the tip 10 of the shaft 2, or it may receive position and orientation information of the tip 10 of the shaft 2 already computed by the system through a processor 3 embedded in the apparatus itself.

Figure 5:
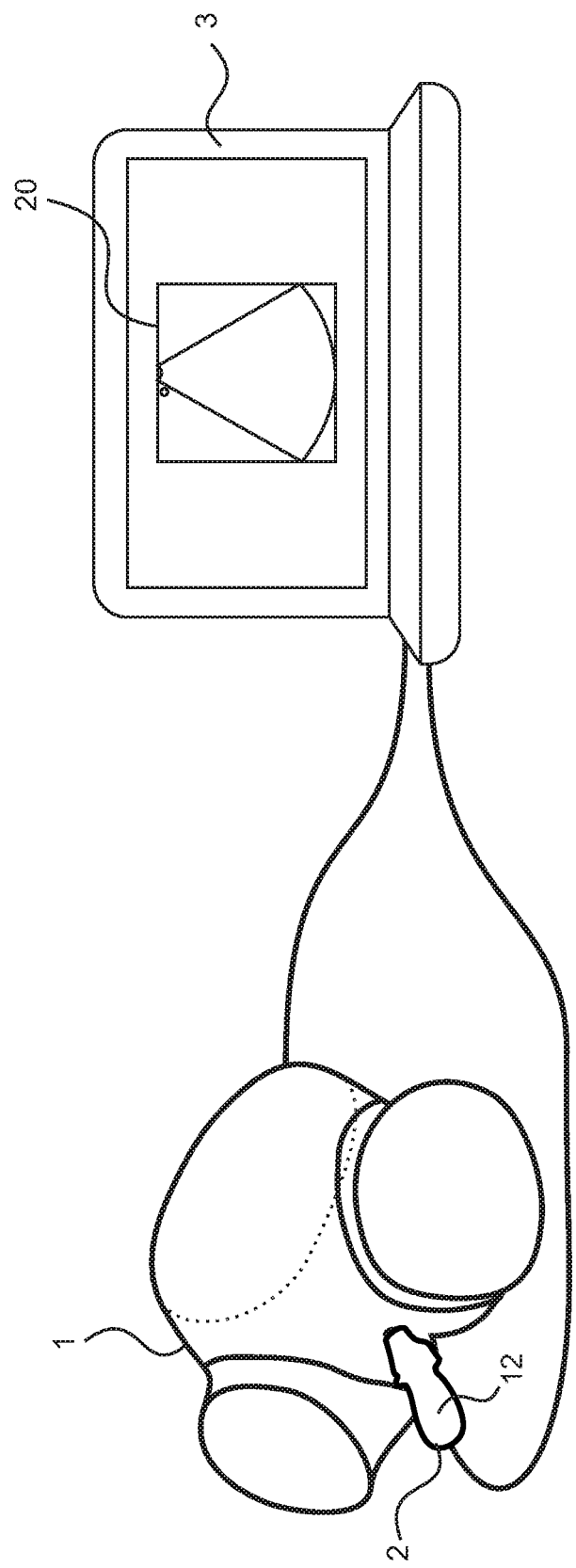
FIG. 5 is a perspective view of an embodiment of the present invention.
Figure 7:
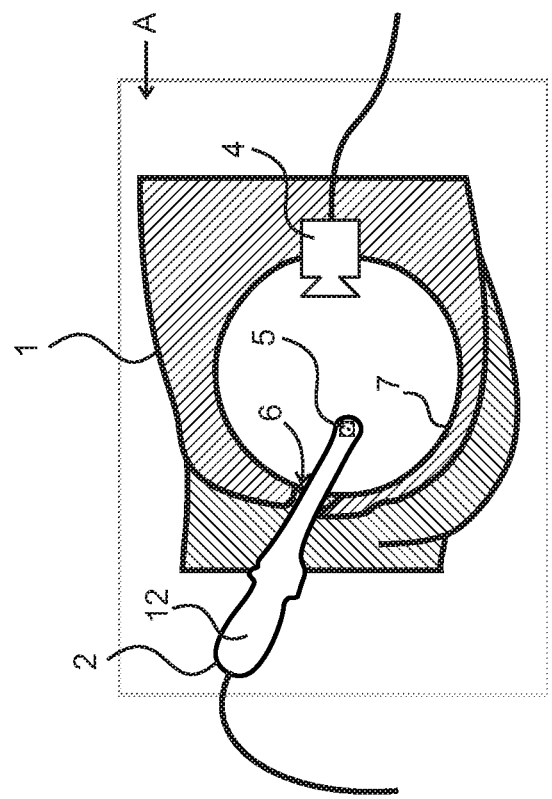
FIG. 7 is a cross-sectional view of a chamber taken at plane A shown in FIG. 6.
Figure 6:
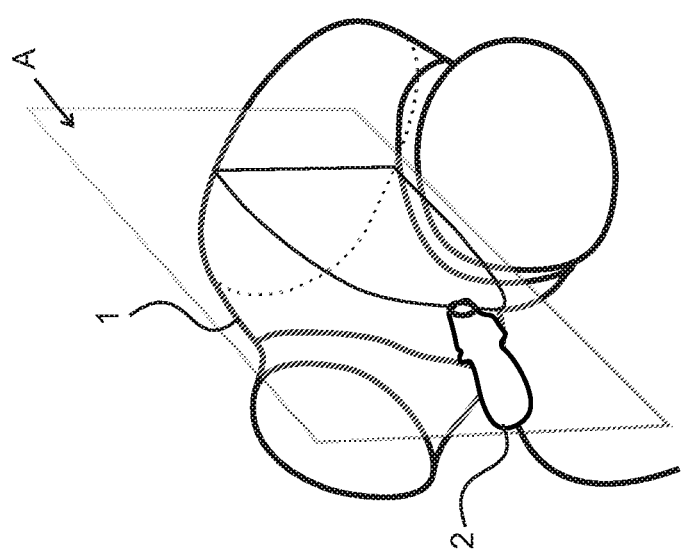
FIG. 6 is a perspective view of an embodiment of the present invention.
Figure 8:
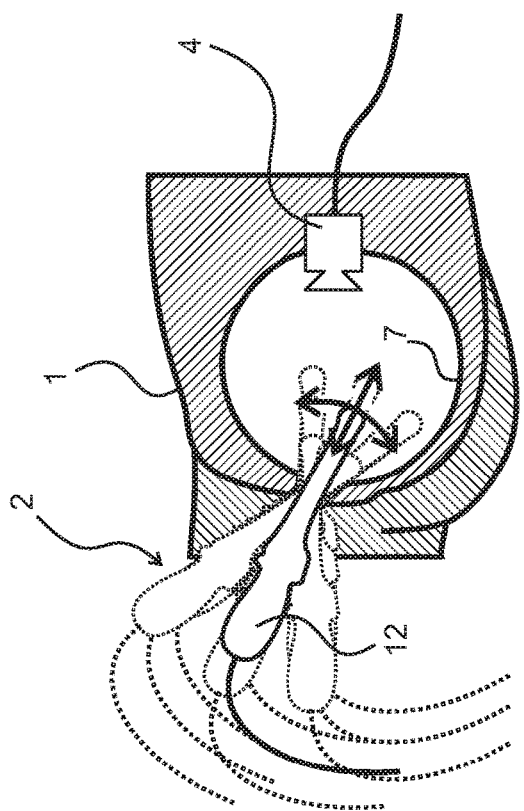
FIG. 8 is the cross-sectional view shown in FIG. 7 showing movement of the shaft (as indicated by the broken lined shafts).
Figure 9:
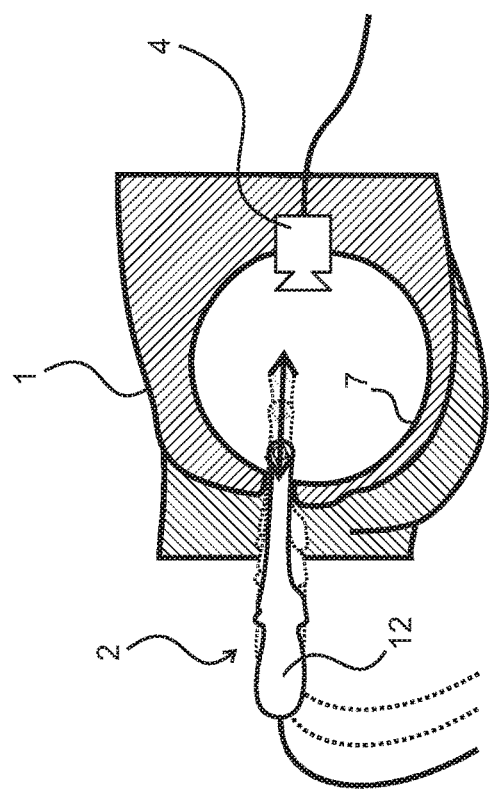
FIG. 9 is the cross-sectional view shown in FIG. 7 showing insertion and withdrawal movement of the shaft (as indicated by the broken lined shafts).
Figure 10:
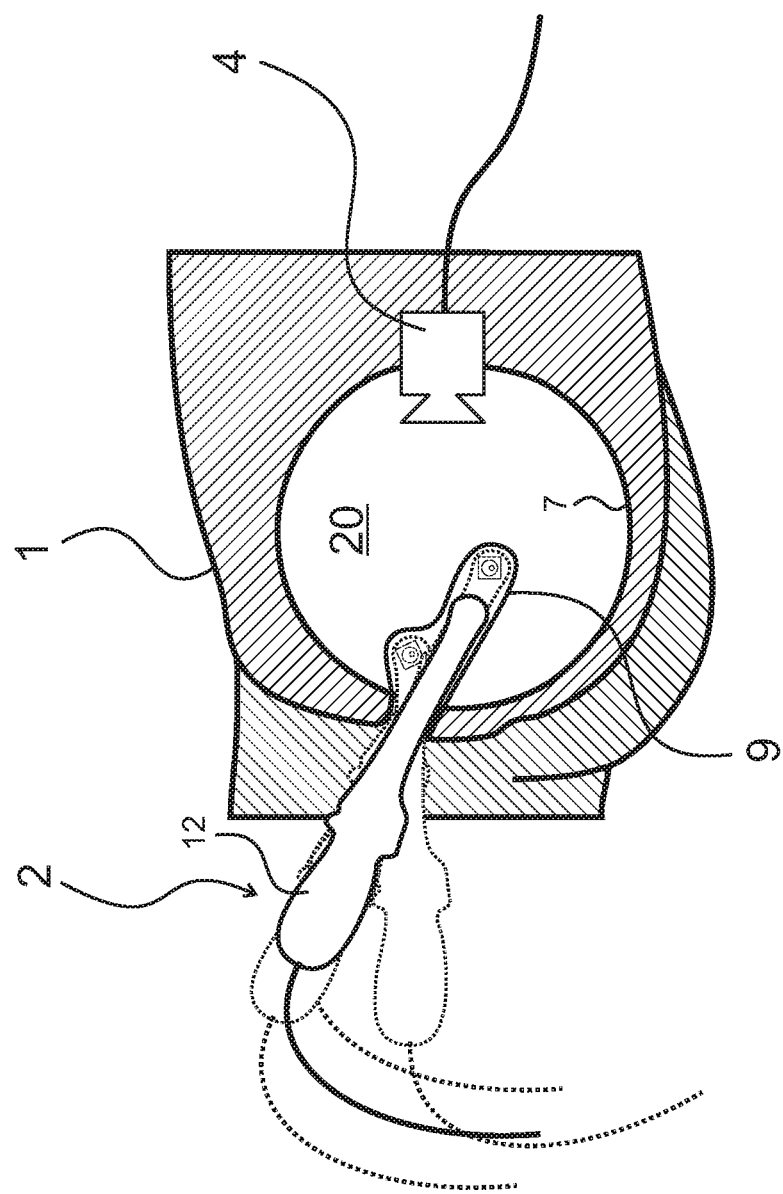
FIG. 10 is the cross-section view shown in FIG. 7 showing movement of the shaft in a chamber containing filler material.

The computing device 3 transmits the position and orientation of the tip 10 of the shaft 2 to the ultrasound simulator and, in turn, the ultrasound simulator updates the visualization to display an ultrasound image 20 that corresponds to the exact spatial configuration of shaft 2 as if it were a real endolumenal probe inserted into a real patient as shown in FIG. 5.

Additionally, if shaft 2 is endowed with controllers 11, the operator may alter the state of the ultrasound simulator by interacting with controllers 11. In the latter, the shaft 2 must have the ability to transmit the state of the controllers 11 to the computing device 3. For example, the operator turn a knob to steer the tip 10 of the probe and the corresponding simulated ultrasound image 20 in the ultrasound simulator, or may press a button to switch the selected case from the available case library.

In use, the training system monitors movement of a marker on a distal end of a shaft with a camera, wherein the distal end of the shaft is inserted inside a chamber through an orifice of the chamber; and determines a position and orientation of the shaft based on the movement of the marker with a processor operatively connected to the camera. In some embodiments, movement of the shaft is restricted with a motion limiter. The position and orientation of the shaft can be calculated using an algorithm or a look up table. The movable shaft 2 can be partially inserted into the orifice 6 of the chamber 1 where the optical camera 4 and light source 8 reside. Once inserted, movement of the part of the movable shaft 2 that is outside the chamber 1 (i.e., the handle 12) results with the movement of the part of the movable shaft 2 that is inside the opaque chamber 1 and that has marker 5 (i.e., the tip 10). The movable shaft 2 may be guided (constrained) by the motion limiter 9. The light source 8 illuminates the chamber 1 to allow movement of the marker 5 to be captured by the camera 4. The images of the marker 5 captured by camera 4 can be processed by a computer processor 3 to calculate corresponding movement of the movable shaft 2.

When an operator moves the shaft 2 by manipulating it from the outside of the chamber 1, the shaft 2 transmits the motion of the operator to the optical marker 5 that is rigidly attached to the end of the shaft 2 hidden inside the chamber 1.

Camera 4 observes the marker 5 as it moves, and transmits its frame data to the processor 3. The processor 3 employs an algorithm that correlates the observations of the marker 5 and its perspective distortions to the position and orientation of shaft 2. Further processing by means of mathematical transformations known to those skilled in the art allows the algorithm to determine the exact position and orientation of the distal tip 10 of the shaft 2 that is hidden inside the chamber 1 in three-dimensional space when in use.

EXAMPLES

Pelvic Trainer

In one embodiment, the system emulates transvaginal sonography (TVS) and/or rectal endoscopic sonography (RES) as shown in FIGS. 5-10 with the shaft 2 mimicking a probe. The endolumenal ultrasound trainer comprises an external mold that mimics the shape of a pelvis that hides an internal hollow chamber 1; a shaft 2 that resembles a transvaginal/transrectal probe; an orifice 6 that allows insertion of the probe 2 into the internal hollow chamber 1; one or more optical markers 5 affixed to the tip 10 of the probe 2; one or more optical cameras 4; and one or more sources of light 8. The optical camera 4 acquires observations of the optical marker 5 and sends them directly to an external computation device 3 that hosts an ultrasound simulator capable of displaying transvaginal/transrectal sonographic images 20. The operator manipulates the probe as they would do in a real OB-GYN or RES clinical session with a real patient. In response to the operator's motions, the ultrasound simulator on computing device 3 displays an ultrasound image 20 that realistically emulates the image the operator would see if they placed the transvaginal/transrectal probe inside a patient at the same position and orientation inside the body of the patient.

Marker 5 may be a small disc with a pattern portraying two fully overlapping but non-concentric circles of contrasting colors. The offset between the circles breaks the symmetry of the pattern and ensures that each observation of the optical marker 5 determines the pose of the probe unambiguously. Alternatively the marker 5 may be a rectangular tile with a pattern portraying a collection of squares of contrasting color arranged in a non-symmetric fashion.

The algorithm running on the processor first isolates the pixels corresponding to optical marker 5 based on their distinct appearance. The algorithm then analyzes the pixels corresponding to marker 5 to determine how the lens of camera 4 has applied a perspective distortion to the observed shape of the marker 5. Given a set of camera parameters known in advance, the perspective distortion alters the size and shape in ways that can be predicted accurately.

In general if the marker 5 is designed appropriately, there is only one possible position and orientation of the marker 5 in three-dimensional space that matches the view of marker 5 seen by the camera 4. The algorithm calculates this position and orientation using techniques known to those skilled in the art.

The shape of orifice 6 and the channel that guides probe 2 into chamber 1 act as a motion limiter 9 that mechanically constrains probe 2. The orifice 6 and channel may be replaceable to simulate different kinds of medical procedures. For example, TVS procedures may require less constrained probe rotations than RES procedures. An extended motion limiter 9 can be inserted inside the chamber 1 to mimic the internal anatomy of the cavity (patient-specific or procedure-specific). Furthermore, one may employ one or a multitude of filler material 20 to fill the empty volume inside the chamber 1 to provide physical resistance to the probe's 2 motion and emulate the haptic feedback of inserting a transvaginal or transrectal probe inside the body cavity. The filler material 20 may have the consistency of a deformable solid or a viscous fluid. For example, the filler material 20 can be an optically transparent and deformable material. In some embodiments, the filler material 20 can be a plurality of small, loose particles packed inside the chamber 1.

TEE Trainer

Figure 11:
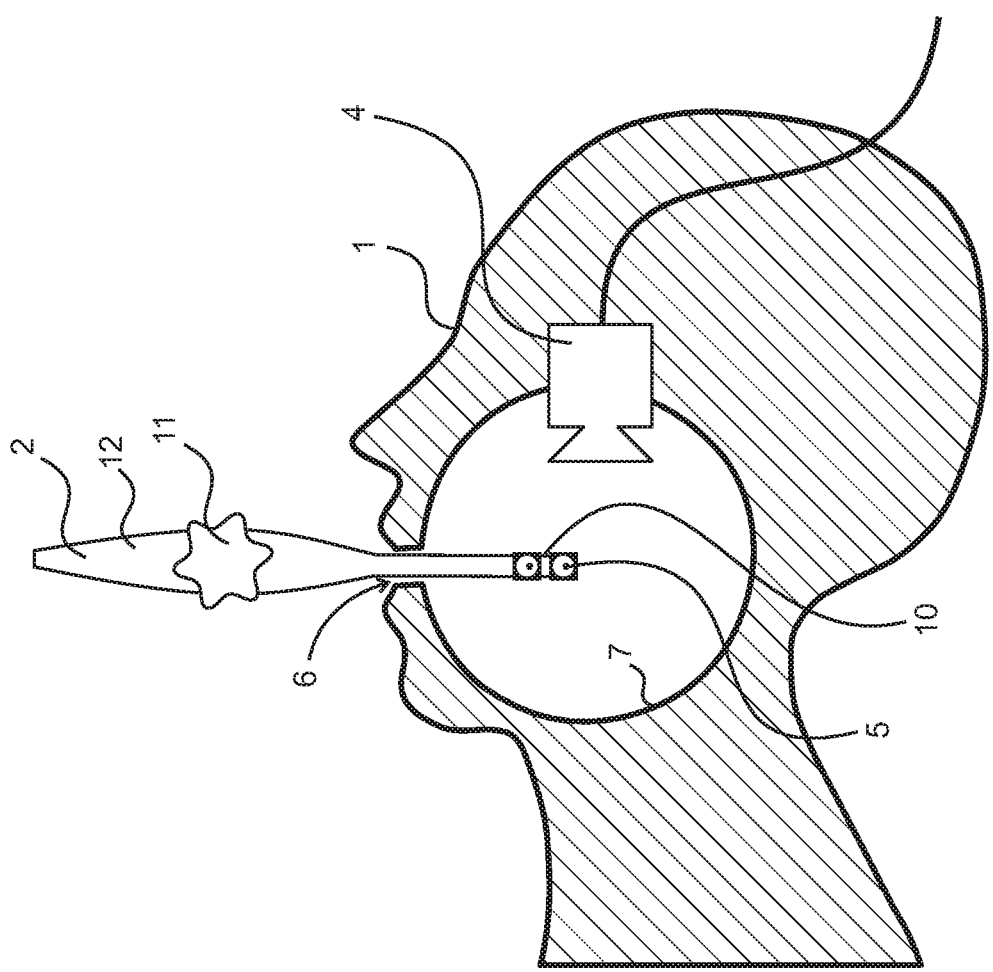
FIG. 11 is a cross-sectional view of a chamber mimicking a human head.

In one embodiment, the system emulates transesophageal echocardiogram (TEE) sonography as shown in FIG. 11 with the shaft 2 mimicking a probe. The trainer comprises a chamber 1 that mimics the shape of a human head with a cavity that corresponds to the inside of the mouth; shaft 2 resembles a real transesophageal probe and is inserted into chamber 1 through an orifice 6 at the mouth; a source of light 8 and a camera 4 are located inside chamber wall 7. Probe 2 has control knobs 11 that mimic the real steering controls of a TEE probe. Probe 2 has a flexible tip 10 that is actuated mechanically in response to control knobs 11 and one or more optical markers 5 are affixed on it. The position of markers 5 informs the penetration depth (advancing and withdrawing) of probe 2 inside the mouth. If more than one marker 5 is used, the relative position of the markers 5 informs the angle at which the operator has steered the flexible tip 10 via the knob (rotate back/forward, flex to left/right, anteflex/retroflex steering). Camera 4 observes marker 5 and through the processor transmits the computed position and orientation of probe 2 to computing device 3 running a simulator capable of visualizing ultrasound of images of TEE sonography.

IVUS Trainer

Figure 12:
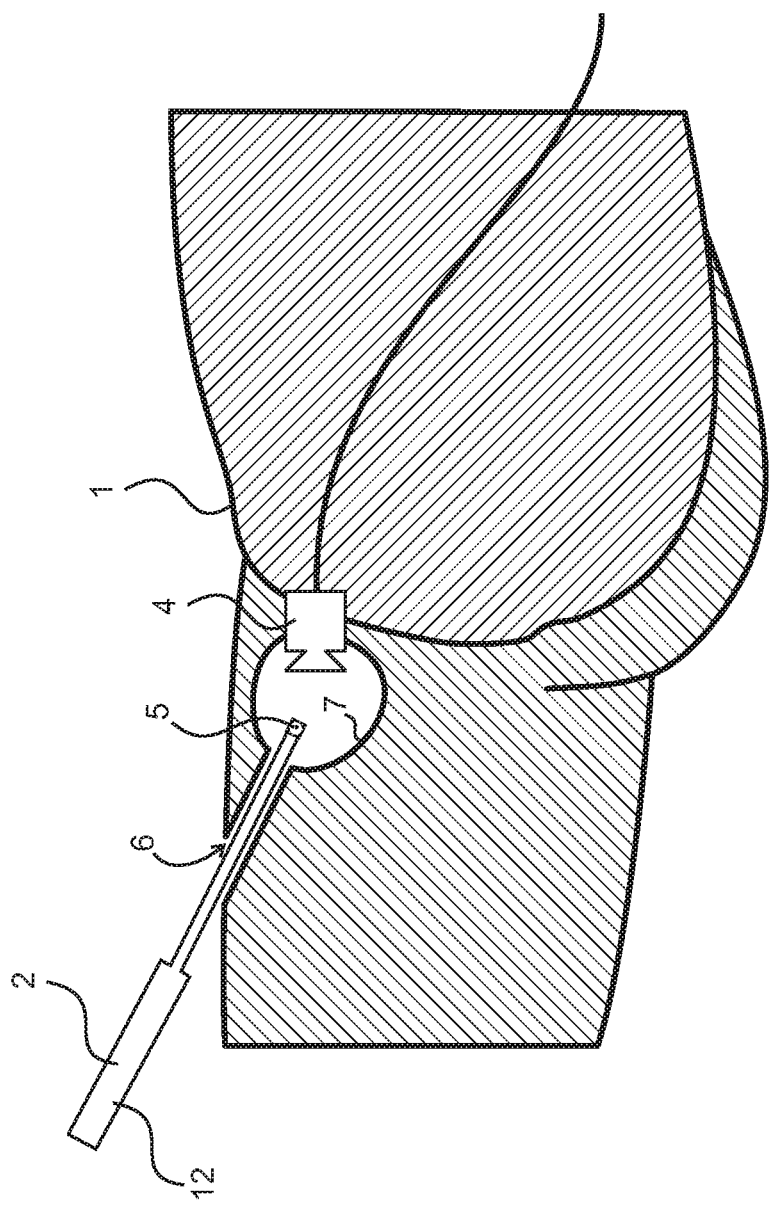
FIG. 12 is a cross-section view of a chamber having an incision.

In one embodiment, the system emulates intravascular ultrasound (IVUS) sonography as shown in FIG. 12 with the shaft 2 mimicking a probe. The trainer comprises a chamber 1 that mimics the shape of a human body or a section of it that is relevant to a particular type of intravascular procedure. A small orifice 6 emulates a puncture into the body and an internal channel 14 leads to a small hollow chamber 1 on the inside. Probe 2 mimics the shape of a real IVUS probe and has the marker 5 attached to its tip 10. Camera 4 is located at one end of internal chamber 1 and observes the marker 5 affixed at the tip of the probe 2. Camera 4 observes the marker 5 and through the processor transmits the computed position and orientation of the probe to computing device 3 running a simulator capable of visualizing ultrasound images 20 of IVUS sonography.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. An ultrasound trainer, comprising:
   a) a chamber defining an orifice;
   b) a shaft insertable into the orifice of the chamber, the shaft having a proximal end, a distal end opposite the proximal end, a flexible tip at the distal end, and a control knob to bend the flexible tip;
   c) a marker positioned on the shaft at the distal end;
   d) a camera positioned to view inside the chamber towards the orifice;
   e) a processor operatively connected to the camera for processing a position and an orientation of the shaft based on the marker;
   f) a motion limiter connected to the chamber at the orifice;
   g) a filler material inside the chamber;
   h) a light source to illuminate the chamber, wherein the chamber mimics a body.

2. An ultrasound trainer, comprising:
   a) a chamber defining an orifice;
   h) a shaft insertable into the orifice of the chamber, the shaft having a proximal end and a distal end opposite the proximal end;
   c) a marker positioned on the shaft at the distal end;
   d) a camera positioned to view inside the chamber;
   e) a processor operatively connected to the camera for processing a position and an orientation of the shaft based on the marker;
   f) a motion limiter connected to the chamber at the orifice;
   g) a filler material inside the chamber; and
   h) a light source to illuminate the chamber, wherein the shaft comprises a flexible tip at the distal end, wherein the shaft comprises a controller to bend the flexible tip.

3. The ultrasound trainer of claim 2, wherein the chamber mimics a body.

4. The ultrasound trainer of claim 3, wherein the body is a vaginal area.

5. The ultrasound trainer of claim 3, wherein the body is a rectal area.

6. The ultrasound trainer of claim 3, wherein the body is a head and neck area.

7. An ultrasound trainer, comprising:
   a) a chamber defining an orifice;
   b) a shaft insertable into the orifice of the chamber, the shaft having a proximal end and a distal end opposite the proximal end;
   c) a marker positioned on the shaft at the distal end;
   d) a camera positioned to view inside the chamber; and e) a processor operatively connected to the camera for processing a position and an orientation of the shaft based on the marker, wherein the shaft comprises a flexible tip at the distal end and, wherein the shaft comprises a controller to bend the flexible tip.

8. The ultrasound trainer of claim 7, further comprising a motion limiter connected to the chamber at the orifice.

9. The ultrasound trainer of claim 8, further comprising a filler material inside the chamber.

10. The ultrasound trainer of claim 9, further comprising a light source to illuminate the chamber.

11. The ultrasound trainer of claim 7, further comprising a filler material inside the chamber.

12. The ultrasound trainer of claim 7, further comprising a light source to illuminate the chamber.

13. The ultrasound trainer of claim 7, wherein the chamber mimics a body.

14. The ultrasound trainer of claim 13, wherein the body is a vaginal area.

15. The ultrasound trainer of claim 13, wherein the body is a rectal area.

16. The ultrasound trainer of claim 13, wherein the body is a head and neck area.

\* \* \* \* \*